(12) United States Patent  
Pinsky

(10) Patent No.: US 7,213,603 B2
(45) Date of Patent: May 8, 2007

(54) SYSTEM AND METHOD FOR TOOTHBRUSH SANITIZATION AND STORAGE

(75) Inventor: Joel Pinsky, New York, NY (US)

(73) Assignee: Violight, Inc., Clearbrook, NY (US)

( * ) Notice: Subject to any disclaimer, the term of this patent is extended or adjusted under 35 U.S.C. 154(b) by 507 days.

(21) Appl. No.: 10/622,788

(22) Filed: Jul. 21, 2003

(65) Prior Publication Data

US 2004/0025899 A1  Feb. 12, 2004

Related U.S. Application Data

(60) Provisional application No. 60/400,775, filed on Aug. 2, 2002.

(51) Int. Cl.
*A61L 2/10* (2006.01)
*A45D 44/18* (2006.01)

(52) U.S. Cl. ............ 132/310; 250/455.11; 250/454.11; 422/24; 422/300

(58) Field of Classification Search .............. 250/455.1
See application file for complete search history.

(56) References Cited

U.S. PATENT DOCUMENTS 3,748,094 A * 7/1973 Sceidell ..................... 312/207
3,820,251 A * 6/1974 Abernathy ..................... 34/60
4,088,445 A * 5/1978 Ellis ............................ 312/207
4,806,770 A * 2/1989 Hylton et al. ........... 250/455.11
4,816,648 A * 3/1989 Dusbabek ................... 219/521
4,888,487 A * 12/1989 Ritter ..................... 250/455.11
4,973,847 A * 11/1990 Lackey et al. .......... 250/455.11
5,023,460 A * 6/1991 Foster et al. ........... 250/455.11
5,029,252 A * 7/1991 Ameseder .............. 250/455.11
5,126,572 A * 6/1992 Chu ....................... 250/455.11

* cited by examiner

*Primary Examiner*—Nikita Wells
(74) *Attorney, Agent, or Firm*—Robert Platt Bell

(57) ABSTRACT

A toothbrush or the like may be inserted, bristles downward, into any of the one or more apertures in a cap removably attached to a body of the apparatus. A peg may be inserted into any one of the apertures in order to allow an electric toothbrush head or other non-standard type of toothbrush to be used. An internal ultraviolet (UV) bulb is located in the apparatus to sanitize the toothbrushes. A timer/control circuit may activate the UV bulb for three minutes and then shut off. To prevent the recurrence of bacterial growth over time, the UV bulb may be automatically reactivated by the timer/control circuit after six hours and activated for another 3 minutes or another amount of time, as programmed. A safety rod may interact with a spring-loaded microswitch coupled to the timer/control circuit to disable the unit if the cap is removed.

20 Claims, 21 Drawing Sheets

SECTION D-D

SECTION A-A

SECTION B-B

SECTION C-C

SYSTEM AND METHOD FOR TOOTHBRUSH SANITIZATION AND STORAGE

CROSS-REFERENCE TO RELATED APPLICATIONS

The present application claims priority from Provisional U.S. Patent Application Ser. No. 60/400,775 filed on Aug. 2, 2002, and incorporated herein by reference.

The present application is related to co-pending Design patent application Ser. No. 29/186,588, filed concurrently herewith, incorporated herein by reference in its entirety.

FIELD OF THE INVENTION

The present invention relates to an apparatus for sanitizing and storing toothbrushes. In particular, the present invention is directed toward a an apparatus which uses a germicidal ultraviolet light to sanitize toothbrushes when the toothbrushes are stored therein.

BACKGROUND OF THE INVENTION

The use of ultraviolet light to sanitize toothbrushes is known in the art. Hylton et al., U.S. Pat. No. 4,806,770, issued Feb. 21, 1989 and incorporated herein by reference, discloses a germicidal toothbrush holder. The apparatus of Hylton includes a substantially closed, upright cylindrical housing having a detachable top lid. The lid has an annular array of openings through which the bristled ends of toothbrushes may be inserted and removed. A UV lamp of low intensity is operably mounted within the housing for emitting ultraviolet radiation in the 200 to 300 nanometer wavelength range, as well as some radiation in the visible range above 300 nanometers and in the ozone producing range below 200 nanometers. A removable cup structure supports the bristled ends of the toothbrushes in an annular array immediately surrounding the lamp, and has an annular interior surface coated with aluminum for high reflectance of UV radiation.

Hylton discloses that his UV lamp is on continuously to expose the toothbrushes to germicidal radiation and to generate small quantities of ozone which accumulate to have some sterilizing effect. However, it is not clear whether the bulb he uses is optimized for best germicidal radiation (253.7 nm) or whether such a battery operated low intensity bulb can provide any appreciable germicidal effect.

The lower portion of the housing is translucent to visible light, so that the holder operates as well as a nightlight for the bathroom. Hylton does disclose a switch for turning off the apparatus, but describes the apparatus operating "continuously". Hylton discloses using a "low intensity" bulb as a safety feature such that if a child removes the cover and peers inside, presumably no eye damage will occur.

However, such a "safety" feature compromises the effectiveness of the apparatus. Moreover, it is not clear than even a "low intensity" bulb would be safe. As the apparatus of Hylton is designed to remain on all night (e.g. as a night light) it consumes energy at all times. Moreover, the user is never apprised as to whether the toothbrushes inserted therein are indeed sanitized. Thus, a requirement remains in the art for better safety features which allow for higher intensity UV bulb usage. In addition, a requirement remains in the art for a sanitizer which is not on all of the time.

Ellis, U.S. Pat. No. 4,088,445, issued May 9, 1978, and incorporated herein by reference, discloses a combination night light and sterilizing holder for toilet articles. A hollow body member has a plurality of side opening pockets at the upper portion thereof to receive toilet articles such as toothbrushes. The inner ends of the pockets have openings into the interior of the body member providing exposure to sterilizing radiation from an uncoated portion of a light bulb supported within the housing. The light emitted from the coated portion serves as a night light. At the top of the holder is a shelf for supporting containers thereon in inverted relation whereby the containers are also sterilized by the bulb.

As with Hylton, Ellis envisions an apparatus which appears to be on all the time, wasting energy when not in use. Moreover, there do not appear to be any safety features to prevent eye exposure to the uncoated mercury vapor bulb of Ellis. Thus, Ellis does not address the deficiencies of Hylton.

Chu, U.S. Pat. No. 5126,572, issued Jun. 30, 1992, and incorporated herein by reference, discloses a toothbrush holder. A personal health care item in the form of a toothbrush holder is provided comprising means to support one or more toothbrushes, and an ultraviolet irradiating light device to treat the brush of any toothbrush mounted within the toothbrush support means and thus kill any germs present within the brush. This novelty toothbrush holder is provided with a switch for activating the apparatus when a toothbrush is inserted. A timer activates the apparatus for 1 to 10 minutes. A battery operated bulb is used.

While the apparatus is provided with a timer and switch, the switch contacts the bristles of the apparatus, possibly spreading contamination between brushes. In addition, no safety features are provided. The novelty aspect of the invention (cartoon heads) invites children to play with the device. Such a device, designed for children should be provided with a "fail-safe" security system.

Abernathy, U.S. Pat. No. 3,820,251, issued Jun. 28, 1974 and incorporated herein by reference, discloses a toothbrush drying device. Toothbrushes are inserted into a housing having a heating device and a source of ultraviolet light. A timer is used to activate the device. Like the other devices cited above using timers, it appears that in Abernathy, once the timer goes off, the light is extinguished until reset. Thus, if a toothbrush is left in the device for an extended period of time, bacteria could grow unchecked.

In addition, there do not appear to be any safety features to this device—it appears it may be opened while in use. In addition, the toothbrushes must be inserted into a rack within a recessed cylinder, with the heads up. It would appear that this would cause unnecessary handling of the toothbrush head, and would also be awkward to use.

Andary et al., U.S. Pat. No. 3,954,407, issued May 4, 1976 and incorporated herein by reference, discloses an automatic toothbrush sterilizer. Andary provides a safety mechanism in that the toothbrushes are inserted into the device and then rotated into place before a sanitizing lamp.

It appears that Andary leaves the UV light on all the time, except when a toothbrush is inserted or removed from the apparatus. Moreover, the rotary chamber design is not user friendly, as the user must rotate the apparatus chamber to insert and release toothbrushes—possibly why Andary envisions a wall-mounted device. The apparatus is also fairly complex, and thus expensive to produce.

Moreover, all of the aforementioned apparatus doe not provide any means for sanitizing anything other than a traditional toothbrush. Modern electric toothbrushes may be provided with removable heads and the like. Such removable heads are not readily adaptable to the toothbrush sanitizers of the Prior Art.

In addition, the various apparatus discussed above do not appear to be easy to clean. As toothbrushes tend to drip water, unused toothpaste, and the like, toothbrush holders tend to accumulate unsavory gunk over time and need to be periodically rinsed. The devices discussed above do not appear to be readily cleaned.

The Andary device, for example, provides an elaborate safety mechanism to prevent UV light from reaching the user. However, this apparatus does not appear to be easily disassembled or cleaned. A device which can be readily taken apart presents obvious UV safety hazards to the user. Thus, the two conflicting requirements—safety and ease of cleaning—have yet to be addressed in the Prior Art by one apparatus.

Thus, it remains a requirement in the art to provide an apparatus which is relatively simple in design and is easy to use. It remains a further requirement in the art to provide an apparatus which may control the amount of time a UV light is applied to the toothbrushes, without being on all the time or going off after only a few minutes. It further remains a requirement in the art to provide an apparatus with a safety feature to shut the apparatus off if an attempt is made to open the device while in use.

It further remains a requirement in the art to provide a toothbrush sanitizer which may be used with non-traditional toothbrushes and other items such as electronic toothbrush heads and the like. It further remains a requirement in the art to provide a toothbrush sanitizer which may be readily disassembled and cleaned to remove accumulate toothpaste and the like.

SUMMARY OF THE INVENTION

The apparatus of the present invention is provided with one or more apertures in a cap removably attached to a body of the apparatus. In the preferred embodiment four apertures are used, although other numbers of the apertures may be used within the spirit or scope of the present invention. Four apertures were chosen for the preferred embodiment as this represents the maximum number of persons typically sharing an average bathroom.

A toothbrush or the like may be inserted, bristles downward, into any of the apertures. In addition to toothbrushes, the apparatus of the present invention may also receive one or more electric toothbrush head(s) or other apparatus to be sanitized. As will be discussed in more detail below, a removable peg may be inserted into any one of the apertures in order to convert that the aperture for use with an electric toothbrush head or other non-standard type of toothbrush or other apparatus (e.g., child's toothbrush).

Once a toothbrush or toothbrushes are inserted into an aperture a membrane button may be pressed to activate an internal ultraviolet (UV) bulb placed in proximity to the toothbrushes as will be discussed below. The membrane button may comprise a membrane covering a microswitch or other type of switch.

When the membrane button is pressed, a timer/control circuit may be activated. This timer/control circuit may be implemented on an integrated circuit or with discrete components as is known in the art. The timer/control circuit may activate the UV bulb for a first predetermined amount of time (e.g., 3 minutes) and then shut off.

To prevent the recurrence of bacterial growth over time, the UV bulb may be automatically reactivated by the timer/control circuit after a second predetermined amount of time (e.g., 6 hours) and activated for the first predetermined amount of time (e.g., 3 minutes) or another amount of time, as programmed. Thus, for example, every hours, the UV bulb may be activated to restrain the growth of bacteria on the toothbrushes inserted in the apparatus.

Thus, a user may have confidence that the toothbrushes are at a constant state of cleanliness, no matter how long they have been left in the apparatus. Moreover, no intervention is required by the user to automatically reactivate the apparatus over time.

A safety rod may interact with a spring-loaded microswitch coupled to the timer/control circuit to disable the unit if the cap is removed. When the cap is removed, pressure on a safety rod is released, and a spring loaded switch on the circuit board is tripped, deactivating the UV bulb. Thus, unlike the prior art devices discussed above, the present invention will automatically shut off if an attempt is made to open the device while in use.

The cap may be provided with one or more extended portions, one of which may interact with the safety rod such that when the cap is removed, a user cannot merely press the safety rod to activate the device, as the safety rod is recessed into the body of the apparatus. Thus a child cannot remove the cap and press on the safety rod and activate the UV/germicidal bulb, as the safety rod is recessed in the body of the drip cup and the cap must be in place for the safety rod to be depressed.

DETAILED DESCRIPTION OF THE INVENTION

Figure 1:
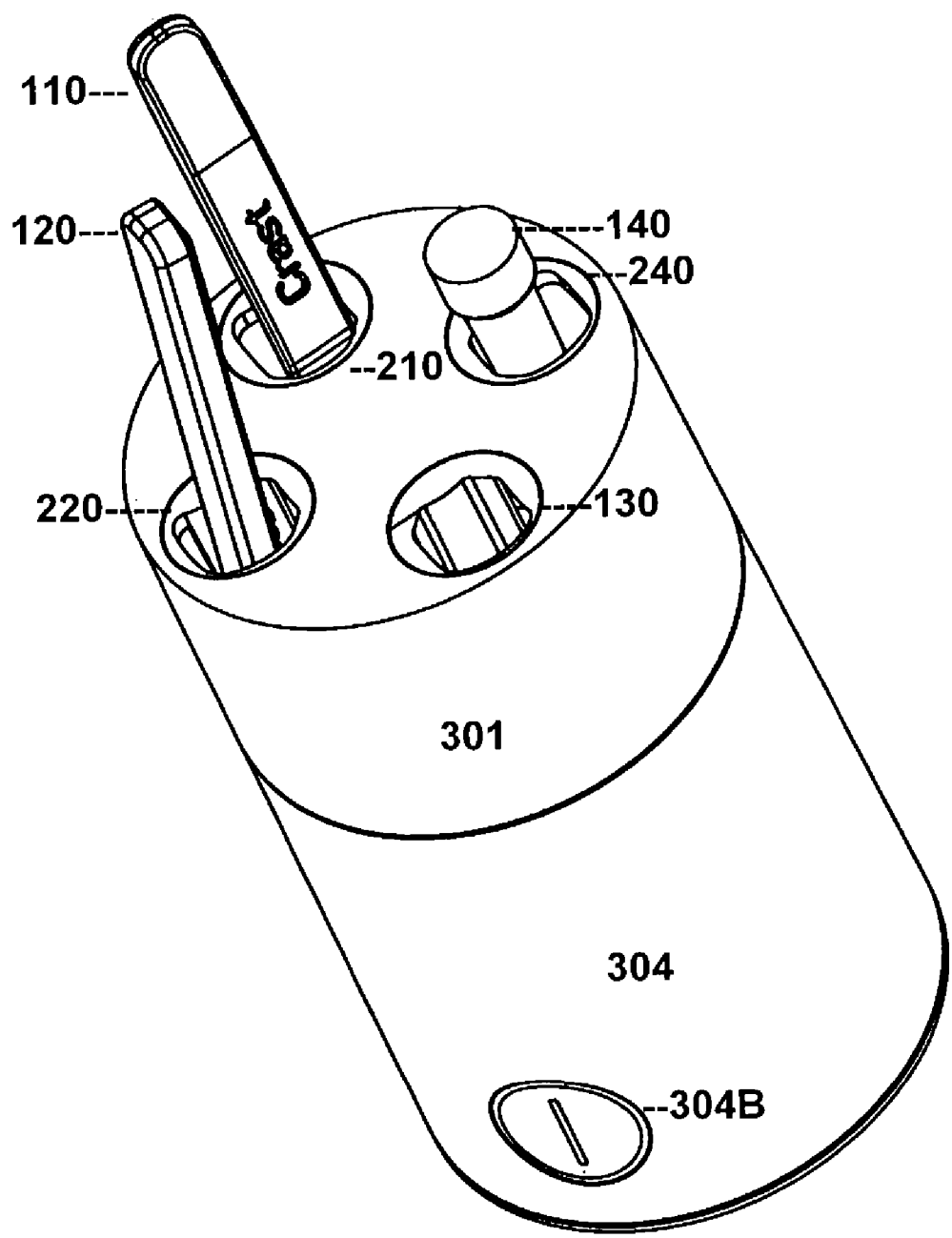
FIG. 1 is a perspective view of the apparatus of the preferred embodiment of the present invention.

FIG. 1 is a perspective view of the apparatus of the preferred embodiment of the present invention. The apparatus of the present invention is provided with one or more apertures 210, 220, 230, and 240. In the preferred embodiment four apertures are used, although other numbers of apertures may be used within the spirit or scope of the present invention. Four apertures were chosen for the preferred embodiment as this represents the maximum number of persons typically sharing an average bathroom.

A toothbrush or the like may be inserted, bristles downward, into any of apertures 210, 220, 230, and 250. In the example illustrated in FIG. 1, two toothbrushes 110, 120 are illustrated inserted into apertures 210, 220. These toothbrushes 110, 120 may comprise any of the type of traditional toothbrushes commercially sold. The apparatus of the present invention may be suitably modified to fit other types of toothbrushes such as those with bent necks and the like.

In addition to toothbrushes, the apparatus of the present invention may also receive one or more electric toothbrush head(s) 140 (or other apparatus to be sanitized), illustrated as inserted into aperture 240. As will be discussed in more detail below, a removable peg may be inserted into any one of apertures 210, 220, 230, 240 in order to convert that aperture for use with an electric toothbrush head or other non-standard type of toothbrush or other apparatus (e.g., child's toothbrush).

Once a toothbrush or toothbrushes are inserted into the apparatus of FIG. 1, membrane button 304B may be pressed to activate an internal ultraviolet (UV) bulb placed in proximity to the toothbrushes as will be discussed below. Membrane button 304B may comprise a membrane covering a microswitch 307B illustrated in FIG. 19, or other type of switch.

When membrane button 304B is pressed, a timer/control circuit 307 (FIG. 20) may be activated. This timer/control circuit 307 may be implemented on an integrated circuit or with discrete components as is known in the art. The timer/control circuit 307 may activate the UV bulb for a first predetermined amount of time (e.g., 3 minutes) and then shut off.

To prevent the recurrence of bacterial growth over time, the UV bulb may be automatically reactivated by the timer/control circuit after a second predetermined amount of time (e.g., 6 hours) and activated for the first predetermined amount of time (e.g., 3 minutes) or another amount of time, as programmed. Thus, for example, every 6 hours, the UV bulb may be activated to restrain the growth of bacteria on the toothbrushes inserted in the apparatus.

Thus, a user may have confidence that the toothbrushes are at a constant state of cleanliness, no matter how long they have been left in the apparatus. Moreover, no intervention is required by the user to automatically reactivate the apparatus over time.

Figure 2:
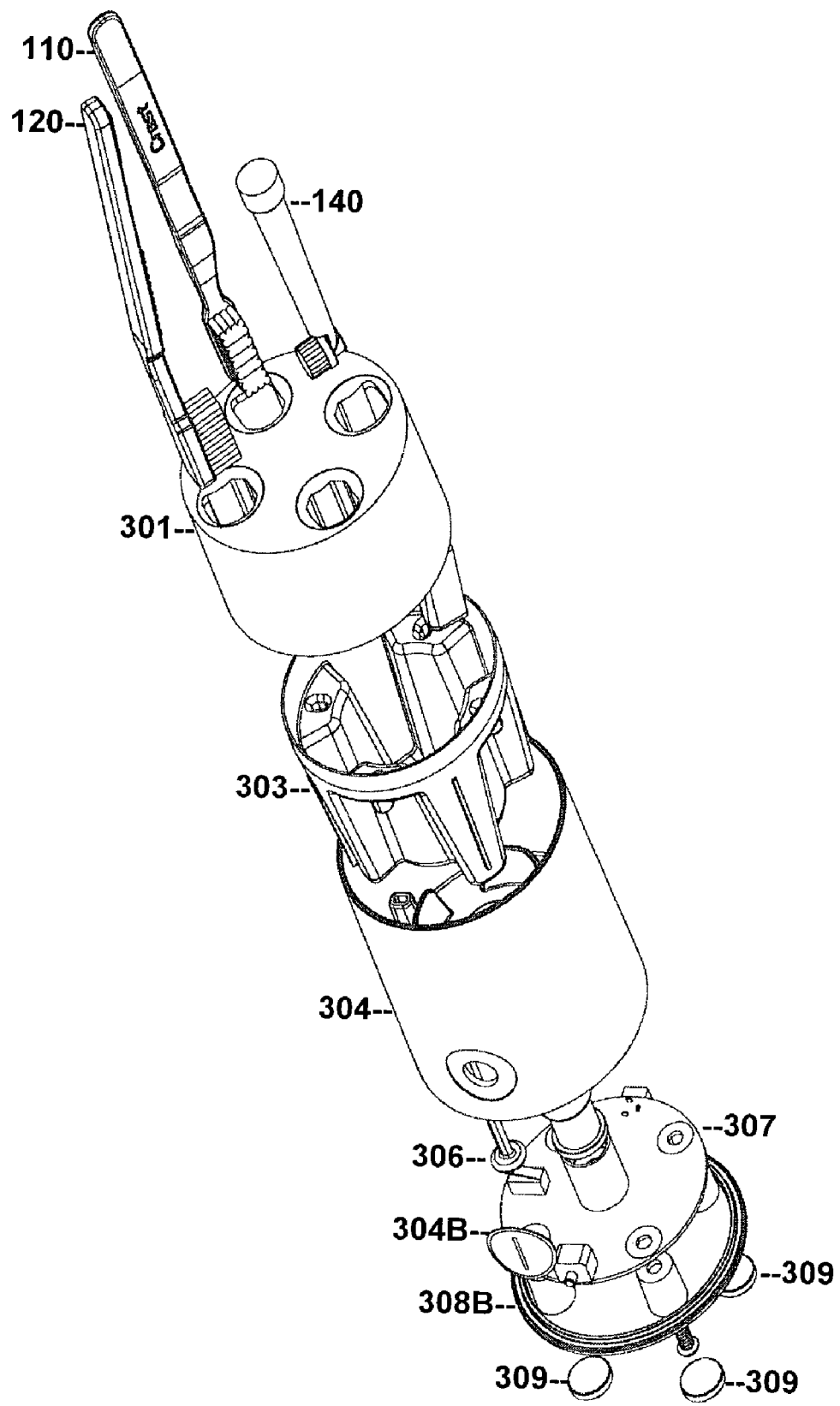
FIG. 2 is an exploded perspective view of the apparatus of the preferred embodiment of the present invention.

FIG. 2 is an exploded perspective view of the apparatus of the preferred embodiment of the present invention. The apparatus comprises several main components as illustrated in FIG. 2, most of which may be fabricated from polycarbonate plastic or the like. Cap 301 contains the apertures 210, 220, 230, and 240 as illustrated in FIG. 1. Body 304 forms the base of the unit and houses most of the components. Cap 301 may be slidably fitted into body 304 such that the apparatus may be readily disassembled by the consumer.

Figure 21:
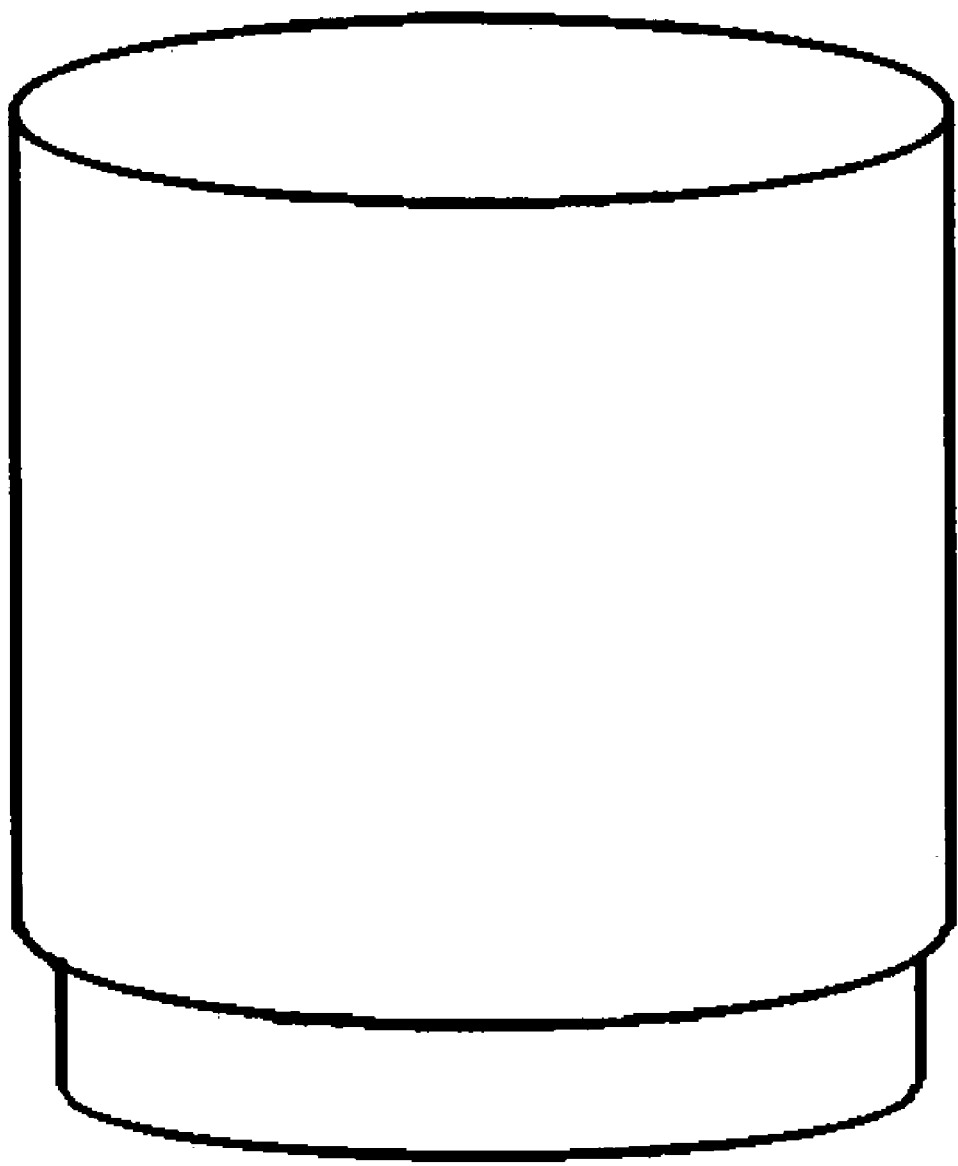
FIG. 21 is a perspective view of a dust cover which may be inserted on the top of the cap of the present invention.

An additional cap, illustrated in FIG. 21 may be slid on top of cap 301 and toothbrushes 110, 120, and 140. This additional cap may be largely cylindrical in shape and may serve to keep dust and dirt out of the unit (and off the toothbrushes) as well as seal off any potential UV leakage from cap 301. The additional cap may be provided with a lip or may be provided with a circumference such that it removably slides over cap 301 or within a groove provided in cap 301 (not shown). The cap of FIG. 21 may also be made of polycarbonate material or other plastic or the like, and may be made, coated, or treated to shield UV radiation. The cap of FIG. 21 may also be used as a rinse cup for brushing teeth.

Removable drip cup 303 may be formed of polycarbonate and treated with a reflective material (aluminized, mylar treatments, or the like) to reflect UV rays around the toothbrushes. Removable drip cup 303 may be provided with a plurality of slots for accepting toothbrushes inserted into apertures 210, 220, 230, and 230. Removable drip cup 303 may be removed by the consumer by removing cap 301 and lifting out removable drip cup 303 from body 304. Removable drip cup 303 may then be rinsed under a faucet and left to dry before reinserting into body 304. In this manner, the apparatus may be readily disassembled and cleaned, unlike the prior art references discussed above.

Figure 3:
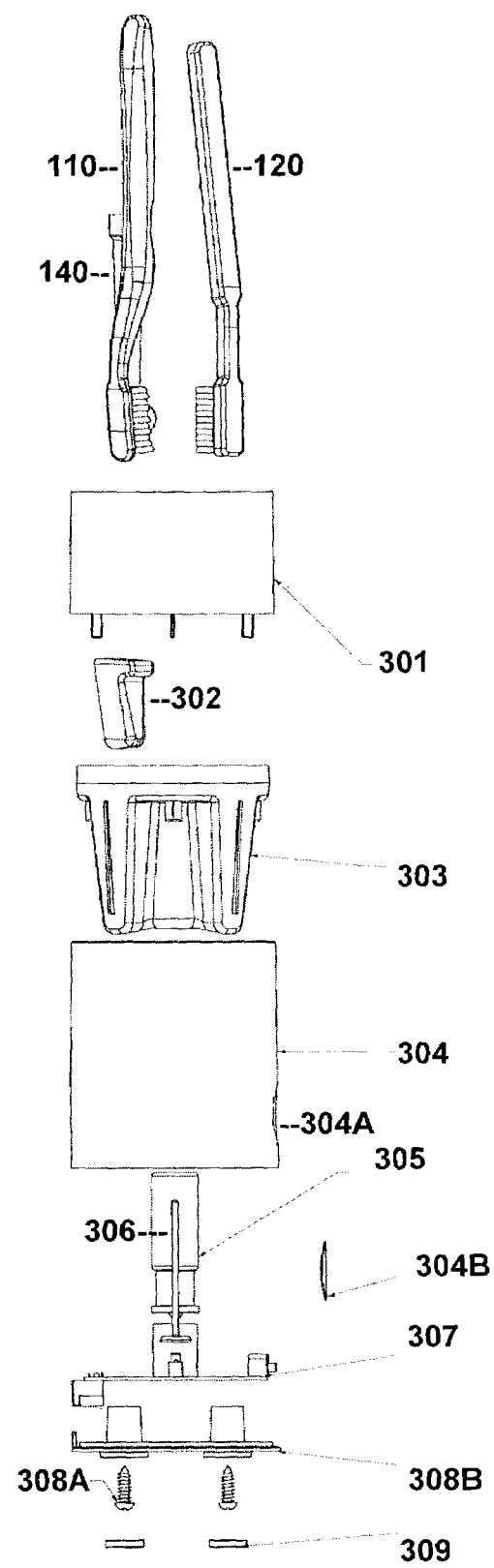
FIG. 3 is an exploded frontal view of the apparatus of the preferred embodiment of the present invention, illustrating the various component parts.

FIG. 3 is an exploded frontal view of the apparatus of the preferred embodiment of the present invention, illustrating the various component parts. As illustrated in FIG. 3, removable height peg(s) 302 may be provided to adjust the depth of one or more of the slots in removable drip cup 303 to modify the device for use with electric toothbrush heads or other devices. By inserting removable height peg(s) 302 into one or more slots of removable drip cup 303, the depth of the slot in removable drip cup 303 is decreased, holding the bristles of an electric toothbrush head (e.g. Braun™ Oral B) for example, near the UV bulb. In this manner, the apparatus of the present invention may accept non-standard toothbrush heads, unlike the prior art references discussed above.

Figure 19:
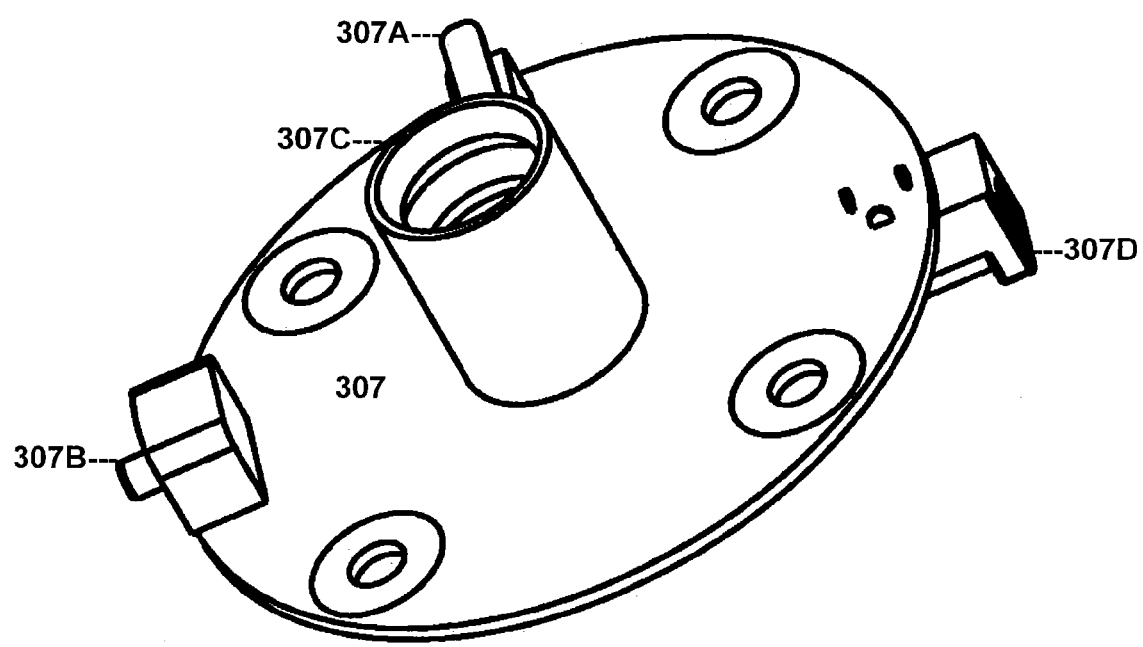
FIG. 19 is a perspective view of circuit board 307 illustrating various components thereof.

Membrane button 304B may be inserted into recess 304A in body 304 and may interact microswitch 307B on circuit board circuit 307 as illustrated in FIG. 19. Circuit board 307 will be discussed in more detail below in connection with FIG. 19. Safety rod 306 similarly interacts with a spring-loaded microswitch (307A in FIG. 19) on circuit board 307 to disable the unit if cap 301 is removed. When cap 301 is removed, pressure on safety rod 306 is released, and spring loaded switch 307A on circuit board 307 is tripped, deactivating the UV bulb. Thus, unlike the prior art devices discussed above, the present invention will automatically shut off if an attempt is made to open the device while in use.

Cap 301 is provided with one or more extended portions 301A (illustrated in FIG. 6), one of which may interact with safety rod 306 such that when cap 301 is removed, a user cannot merely press safety rod 306 to activate the device, as safety rod 306 is recessed into body 304. Thus a child cannot disassemble the apparatus and press on safety rod 306 and activate UV/germicidal bulb 305, as safety rod 306 is recessed in body 304 and cap 301 must be in place for safety rod 306 to be depressed.

UV/germicidal bulb 305 may comprise any one of a number of bulbs known on the market, such as those discussed above in connection with the Prior Art. In the preferred embodiment, a UV bulb emitting radiation at 253.7 nm wavelength is used. Such UV radiation provides a germicidal effect, killing most bacteria and germs. In addition, other types of germicidal bulbs may be used to disinfect items inserted into the apparatus of the present invention, including but not limited to heat bulbs or heat generators, or the like. A waterproofing ring (e.g., neoprene o-ring or the like) may be inserted onto bulb 305 where it screws into socket 307C (FIG. 19) to prevent water from corroding or shorting out socket 307C.

Note that in the preferred embodiment, cap 301 is translucent so that the user can see the UV light action at work. Cap 301 may be made of a material (or suitably coated or the like) to filter out harmful UV rays. In the preferred embodiment, base 304 is made of a translucent material. Of course, both cap 301 and base 204 may be made of other types of materials without departing from the spirit and scope of the present invention.

Base 308 provides support for the apparatus, and also encloses circuit board 307. UV/Germicidal bulb 307 may be attached to circuit board 307 via bayonet fitting, screw socket, plug socket or the like 307C as illustrated in FIG. 19. Screws 308A secure base to body 304 and non skid pads (rubber feet) 309 may cover screws 308A to provide an attractive appearance and also to prevent the apparatus from slipping on a bathroom counter or the like.

Figure 4:
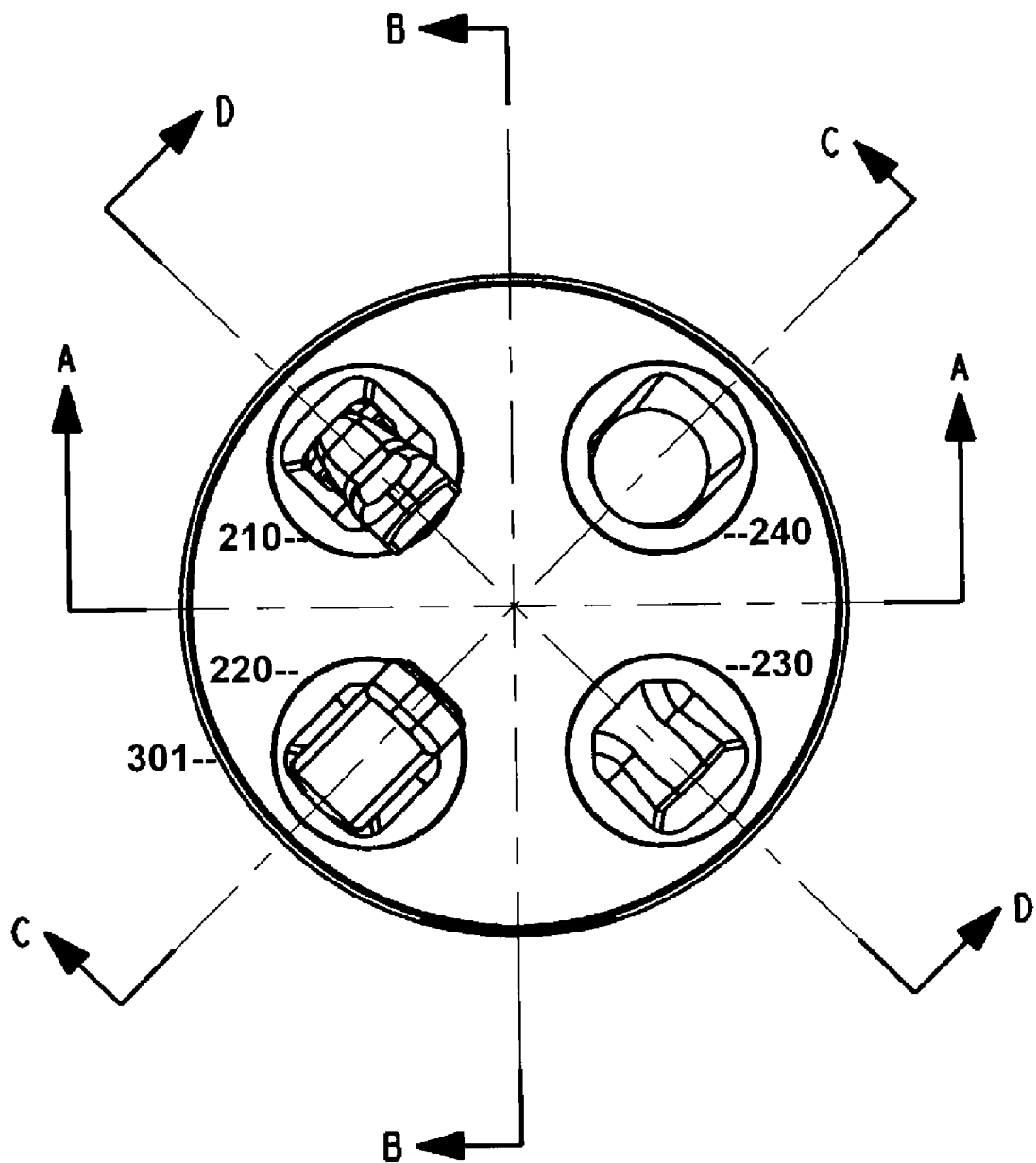
FIG. 4 is a top view of the apparatus of the present invention showing several section lines.

FIG. 4 is a top view of the apparatus of the present invention showing several section lines. These sectional views are illustrated in FIGS. 5–8 and will further aid in understanding the present invention.

Figure 5:
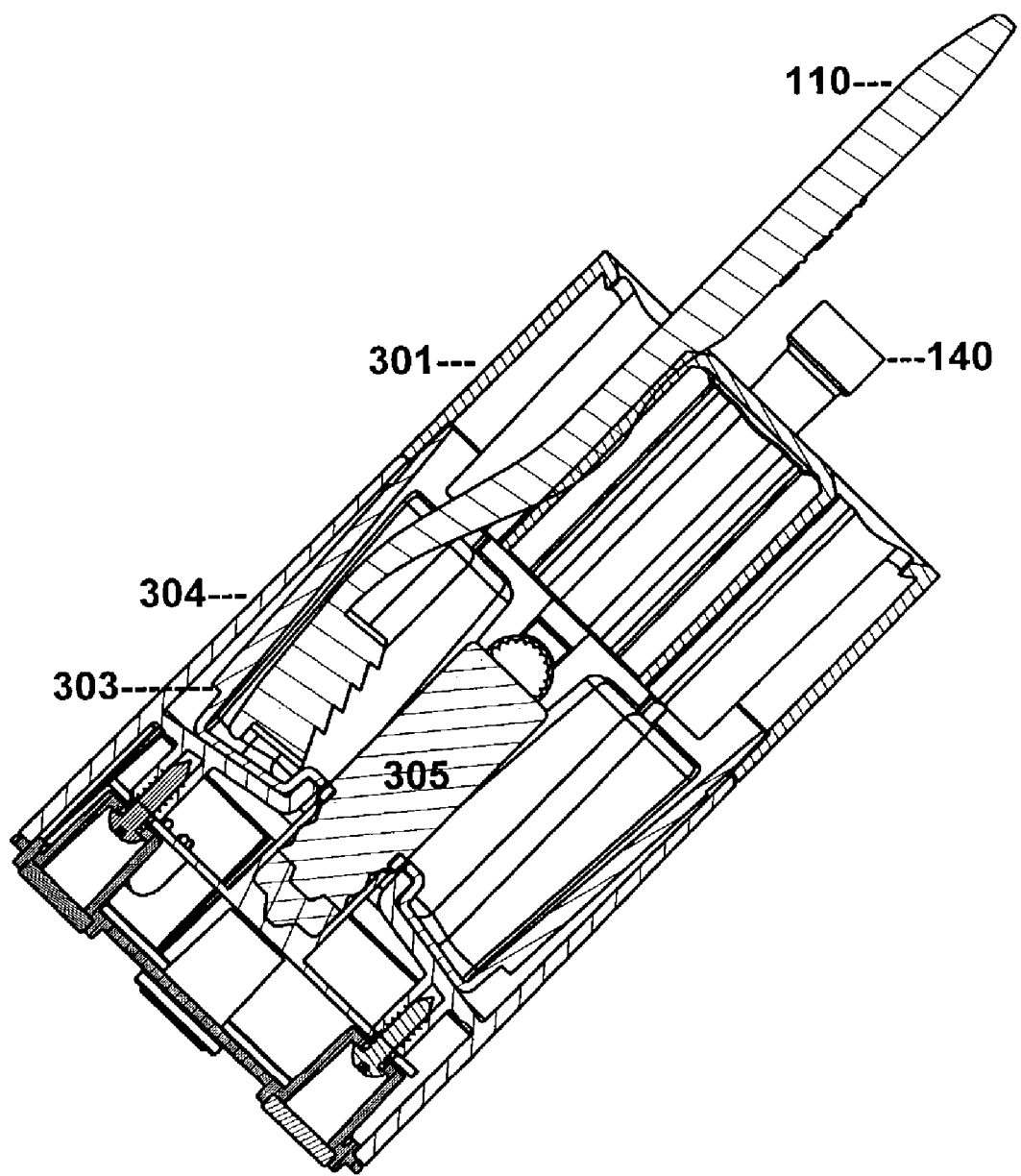
FIG. 5 is a cross-sectional view of the apparatus of the present invention along section lines D—D of FIG. 4.

FIG. 5 is a cross-sectional view of the apparatus of the present invention along section lines D—D of FIG. 4. This Figure illustrates how the bristle end of toothbrush 110 is held in close proximity to UV bulb 305 by drip cup 303. As noted above, drip cup 303 may be coated with a reflective material or made from a material with reflective properties (i.e., aluminum) such that UV rays from bulb 305 are reflected onto the bristle and head portion of brush 110.

Figure 6:
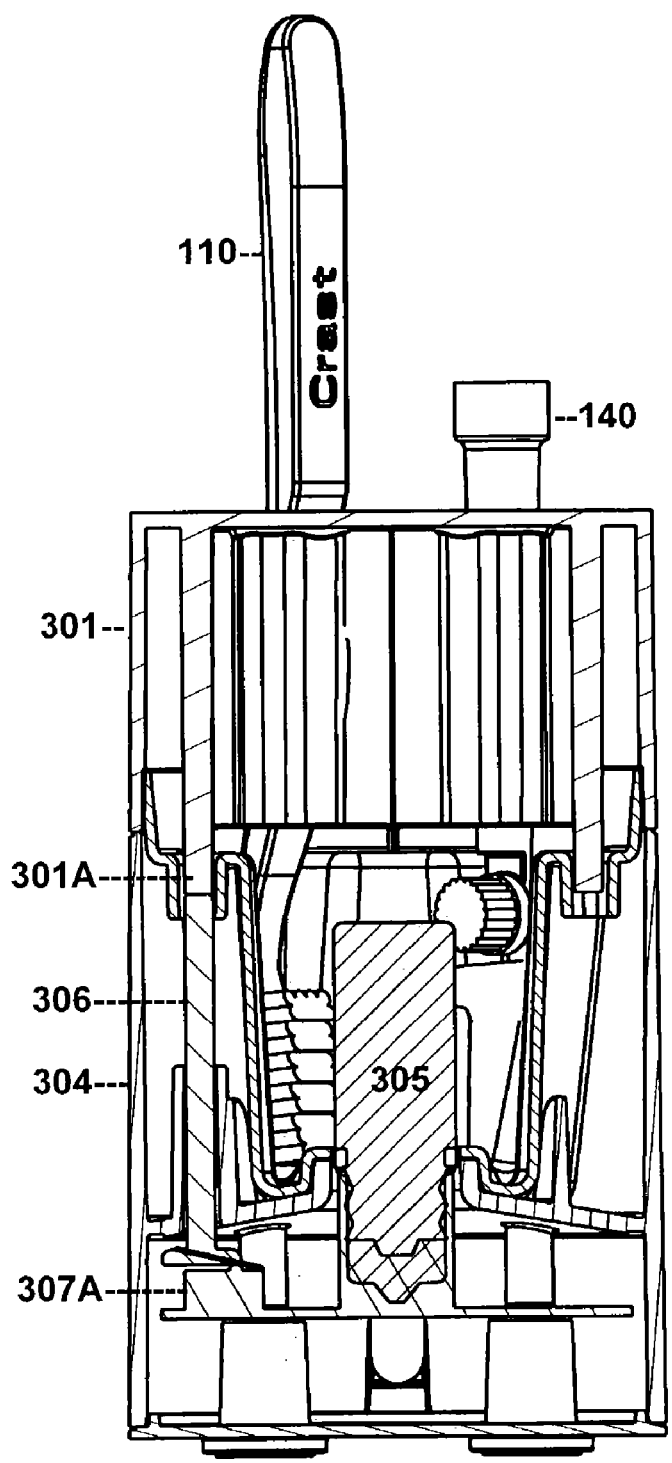
FIG. 6 is a cross-sectional view of the apparatus of the present invention along section lines A—A of FIG. 4.

FIG. 6 is a cross-sectional view of the apparatus of the present invention along section lines A—A of FIG. 4. This Figure illustrates how safety rod 306 is recessed in body 304. Extended portion 301A on cap 301 presses down on safety rod 306 to keep the unit activated. When cap 301 is removed, safety rod 306 is pressed up by action of microswitch 307A, shutting off the unit.

Note that safety rod 306 may be even further recessed and extended portion 301A even further elongated to prevent a user from activating the device when removable drip cup 303 is removed. Note also that extended portion 301A may be made even longer so as to eliminate the need for safety rod 306 altogether, such that extended portion 301A comes in direct contact with microswitch 307A when cap 301 is inserted into body 304.

Figure 20:
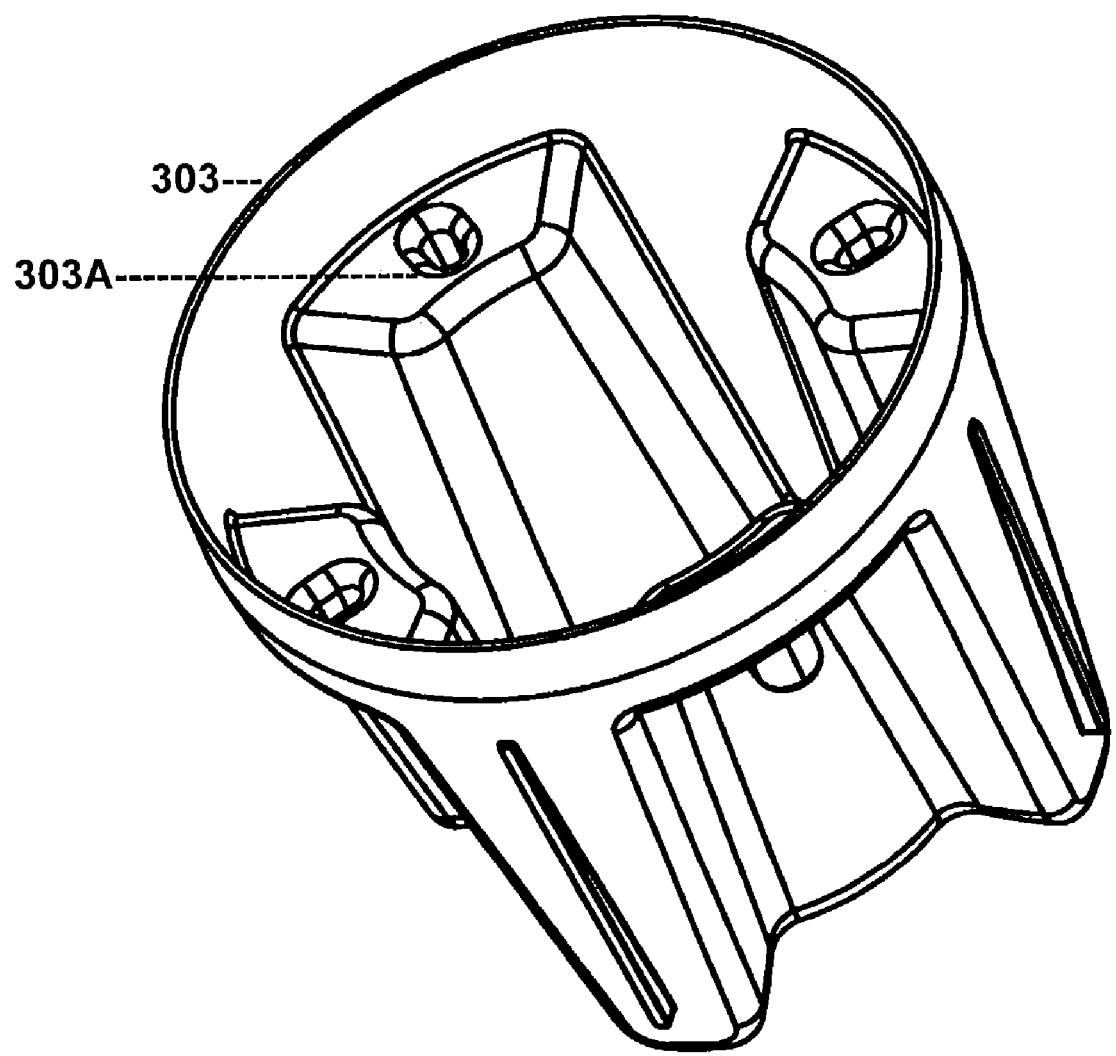
FIG. 20 is a perspective view of the removable drip cup 303.

FIG. 20 is a perspective view of the removable drip cup 303. This Figure provides a better understanding of the three-dimensional shape of removable drip cup 303 and also better illustrates the features of removable drip cup 303. In particular, note that removable drip cup 303 is provided with four holes 303A for accepting safety rod 306. Although only one safety rod 306 is envisioned in the preferred embodiment of the present invention, the use of four holes allows drip cup 303 to be inserted into base 304 in any one of four orientations.

Thus, the user need to struggle to determine which is the "correct" orientation for removable drip cup 303 in order to make the apparatus work. Similarly, cap 301 may be provided with four extended portions 301A such that cap 301 may be inserted into base 204 in any one of four orientations in the preferred embodiment.

Figure 7:
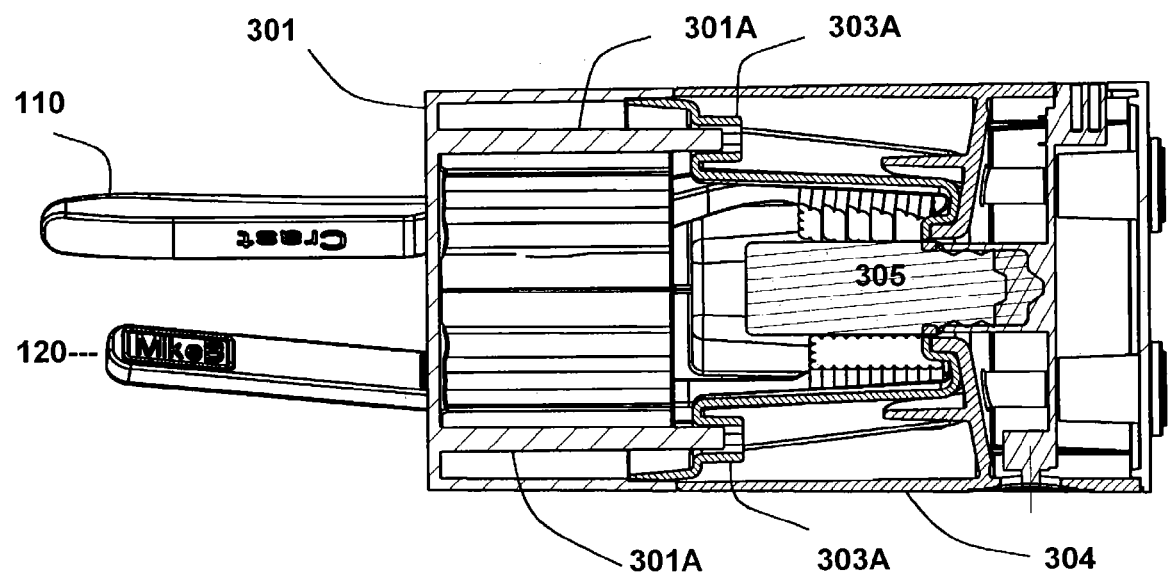
FIG. 7 is a cross-sectional view of the apparatus of the present invention along section lines B—B of FIG. 4.

FIG. 7 is a cross-sectional view of the apparatus of the present invention along section lines B—B of FIG. 4. This Figure illustrates how two of the extended portions 301A fit into holes 303A without interacting with safety rod 306. These extended portions 301A help maintain firm orientation of cap 301 and removable drip cup 303 while still allowing the assembly to be quickly disassembled and reassembled.

Figure 8:
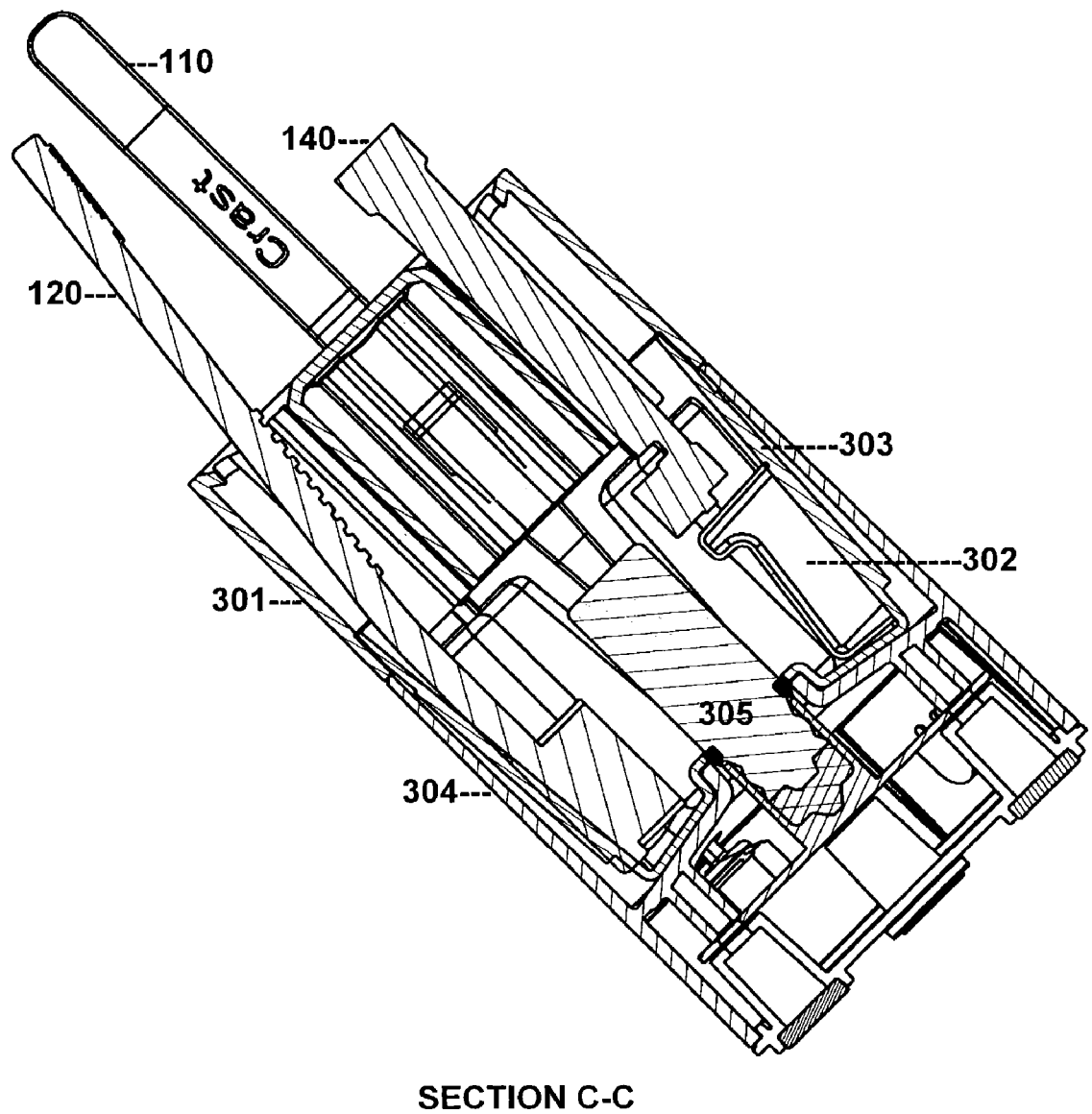
FIG. 8 is a cross-sectional view of the apparatus of the present invention along section lines C—C of FIG. 4.

FIG. 8 is a cross-sectional view of the apparatus of the present invention along section lines C—C of FIG. 4. This Figure illustrates how height peg 302 may be inserted into removable drip cup 3 to allow insertion of non-standard toothbrushes and other devices, such as electric toothbrush head 140. Height peg 302 raises electric toothbrush head 140 such that it does not fall down inside the unit, and also maintains the bristle portion of electric toothbrush 140 in proximity with UV/germicidal bulb 305. Note that the dimensions of height peg 302 may be altered to provide different height pegs 302 of different dimensions for different types of non-standard toothbrushes or other devices to be sanitized in the apparatus of the present invention (e.g., tweezers, toenail clippers, and other personal hygiene devices).

Figure 9:
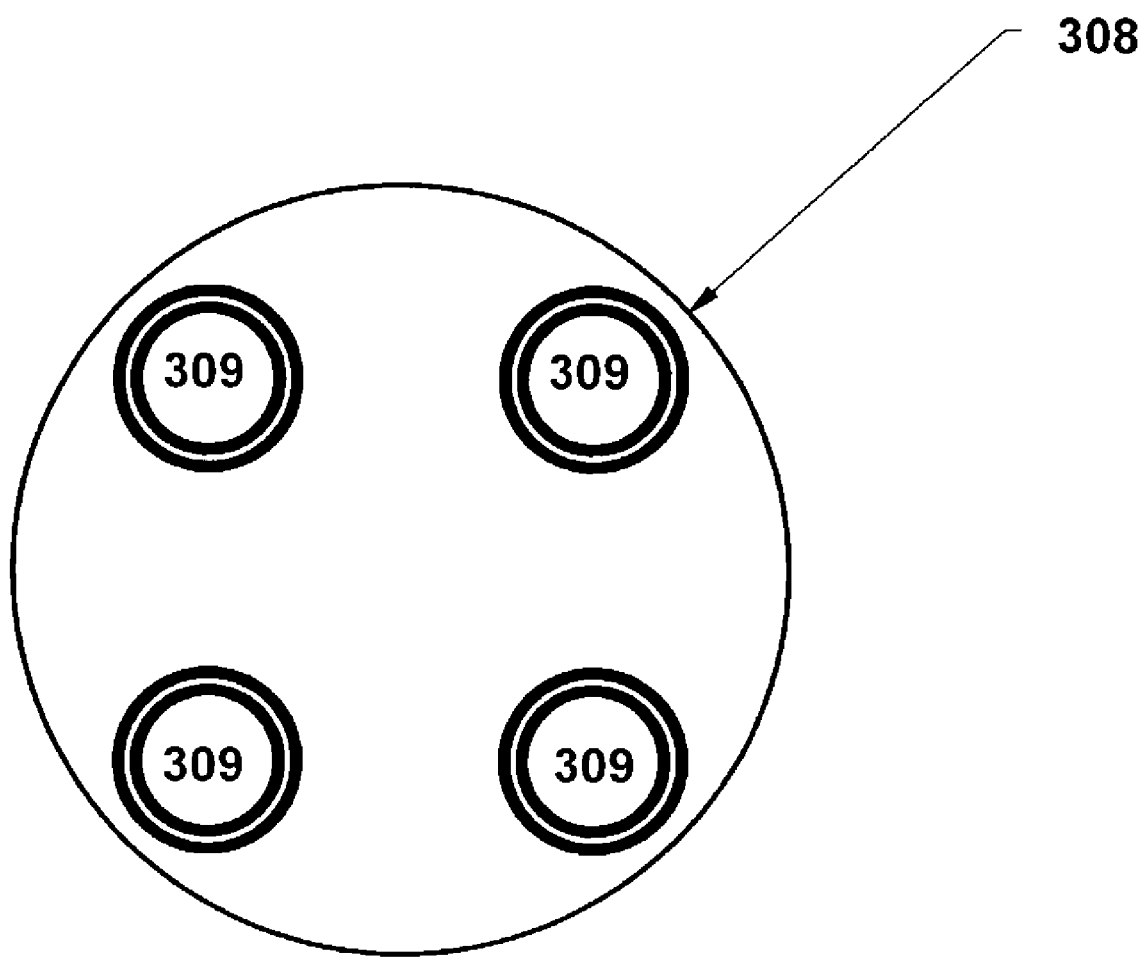
FIG. 9 is a bottom view of the apparatus of the present invention.

FIG. 9 is a bottom view of the apparatus of the present invention, illustrating how non-skid pads 309 are placed in recesses of base 308. Non-skid pads 309 may be commercially purchased items and may be made of a non-marking rubber provided with a contact adhesive backing.

FIG. 19 is a perspective view of circuit board 307 illustrating various components thereof. Circuit board 307 may be a conventional type printed circuit board manufactured using techniques known in the art. Circuit board 307 may be provided with power plug 307D which may accept input power from a wall-pack transformer or the like, typically in low voltage DC form. Power plug 307D may comprise a 2 mm PCB Power Connector, manufactured by CUI, INC, part number PJ-102A.

In an alternative embodiment, a high power lithium battery may be provided to power the circuit board 307 and UV bulb 305. In such an embodiment, the lithium battery may be provided in the space occupied by circuit board 307 and/or be provided mounted to circuit board 307. The activation button may be provided with a lamp (e.g., LED) which will illuminate or flash when a low battery or battery change condition occurs.

Activation switch 307B, as discussed above, is located behind membrane 304B when the unit is assembled. In the preferred embodiment, activation switch 307B may comprise a 6 mm PB-SWITCH RT ANG MOM 150GF manufactured by OMRON Corporation, Part Number B3F-3152.

Microswitch 307A may comprise a spring loaded microswitch which interacts with safety rod 306 when the unit is assembled. The spring loaded feature of microswitch 307A insures that safety rod 306 will be pushed up whenever cap 301 is removed. In the preferred embodiment, microswitch 307A may comprise a LEVER SWITCH PCB SPDT 3A 80GF manufactured by OMRON Corporation, part number D2F-L.

Socket 307C (here illustrated as a threaded socket) accepts UV/Germicidal bulb 305. In the preferred embodiment, socket 307C may comprise a LAMP BASE VERT PCMT E17 manufactured by BULBTRONICS Incorporated, Part Number 4401-002.

Suitable logic components, microprocessor components, or programmable logic array (PLA) components may be provided on circuit board 307 to operate the apparatus of the present invention as described above, or in another programmed mode of operation. The use of microprocessor controls allows the unit to be readily altered for other applications, or to provide different modes of use. In the preferred embodiment of the present invention, programming logic is provided by a MOSFET N-CH LOGIC 25V SOT-23, manufactured by FAIRCHILD SEMICONDUCTOR, part number FDV303N and a Integrated Circuit MicroController 0.5K 4MHZ OTP SO8, manufactured by MICROCHIP, Inc., part number PIC12C508A-04/SM. The programming and layout of such components is known to those skilled in the art.

FIGS. 10–18 illustrate the ornamental external appearance of the present invention as contemplated in the preferred embodiment. The ornamental external appearance of the present invention is claimed in the copending Design Application incorporated by reference above. The ornamental design of the present invention was prepared by renown designer Philippe Starck.

Figure 10:
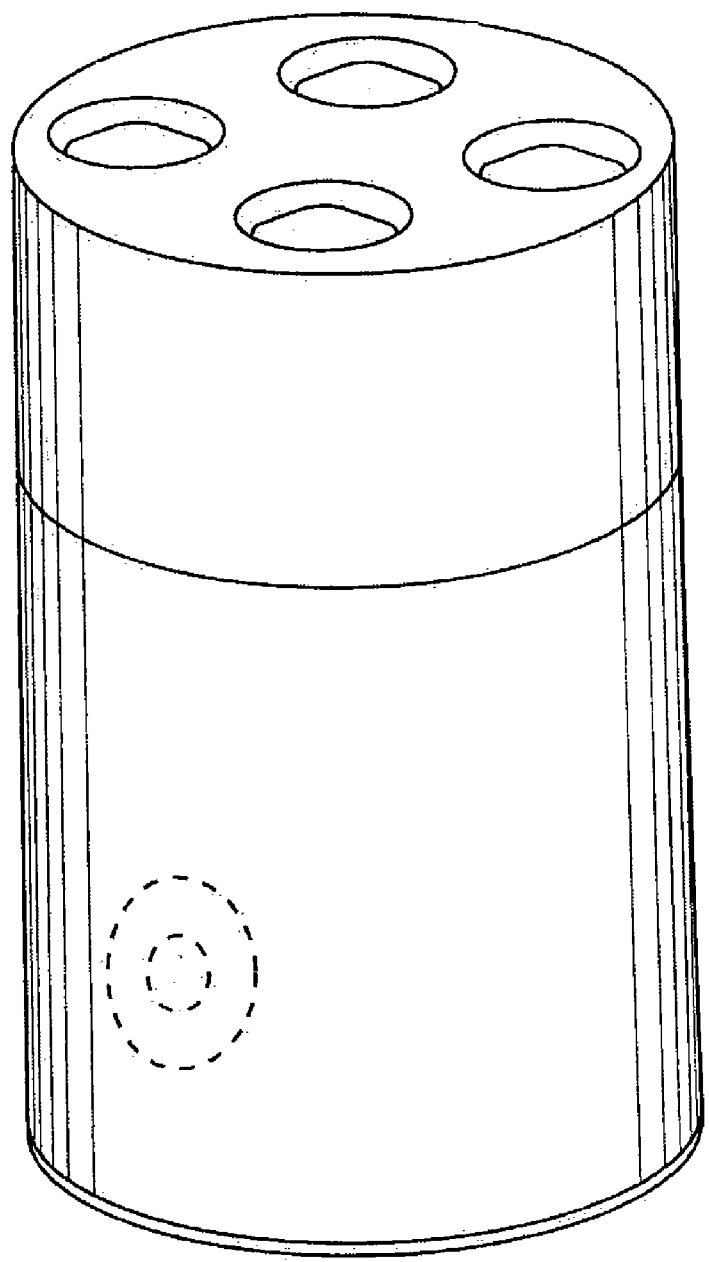
FIG. 10 is a front perspective view of the external appearance of the preferred embodiment of the present invention.
Figure 11:
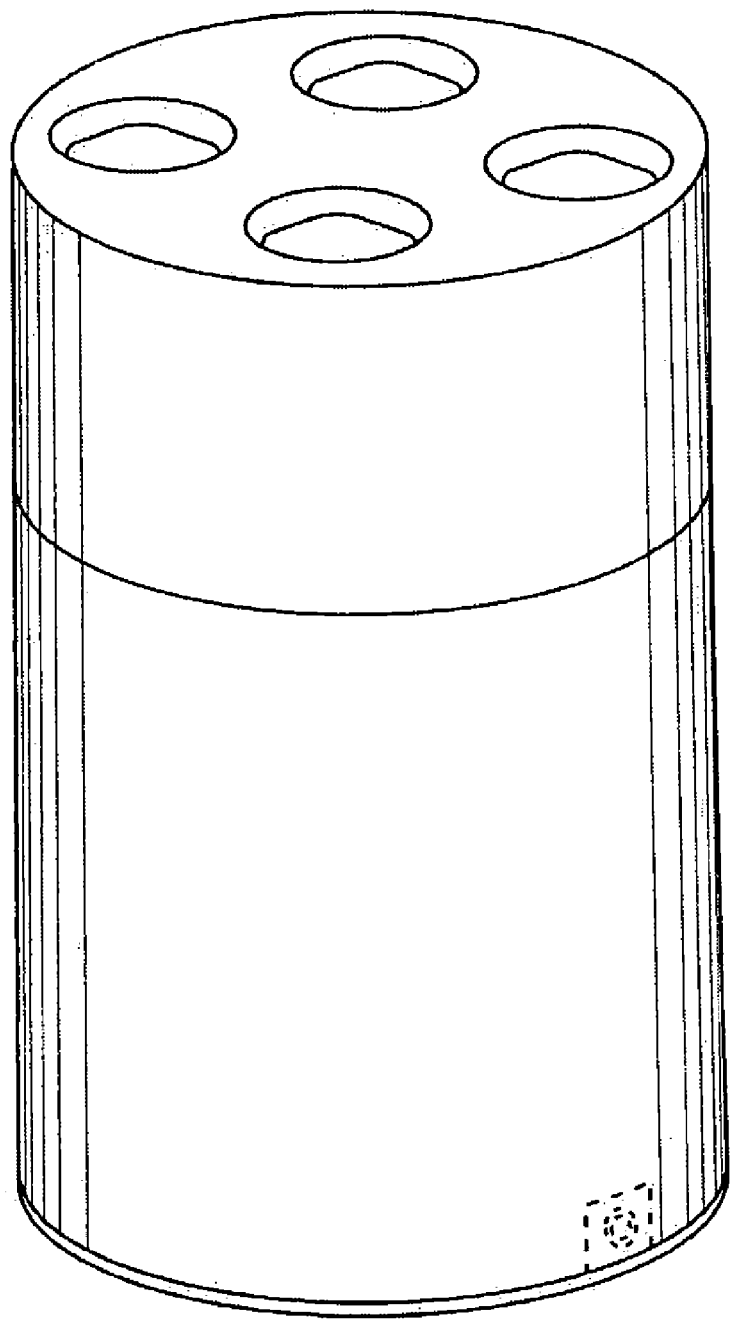
FIG. 11 is a rear perspective view of the external appearance of the preferred embodiment of the present invention.
Figure 12:
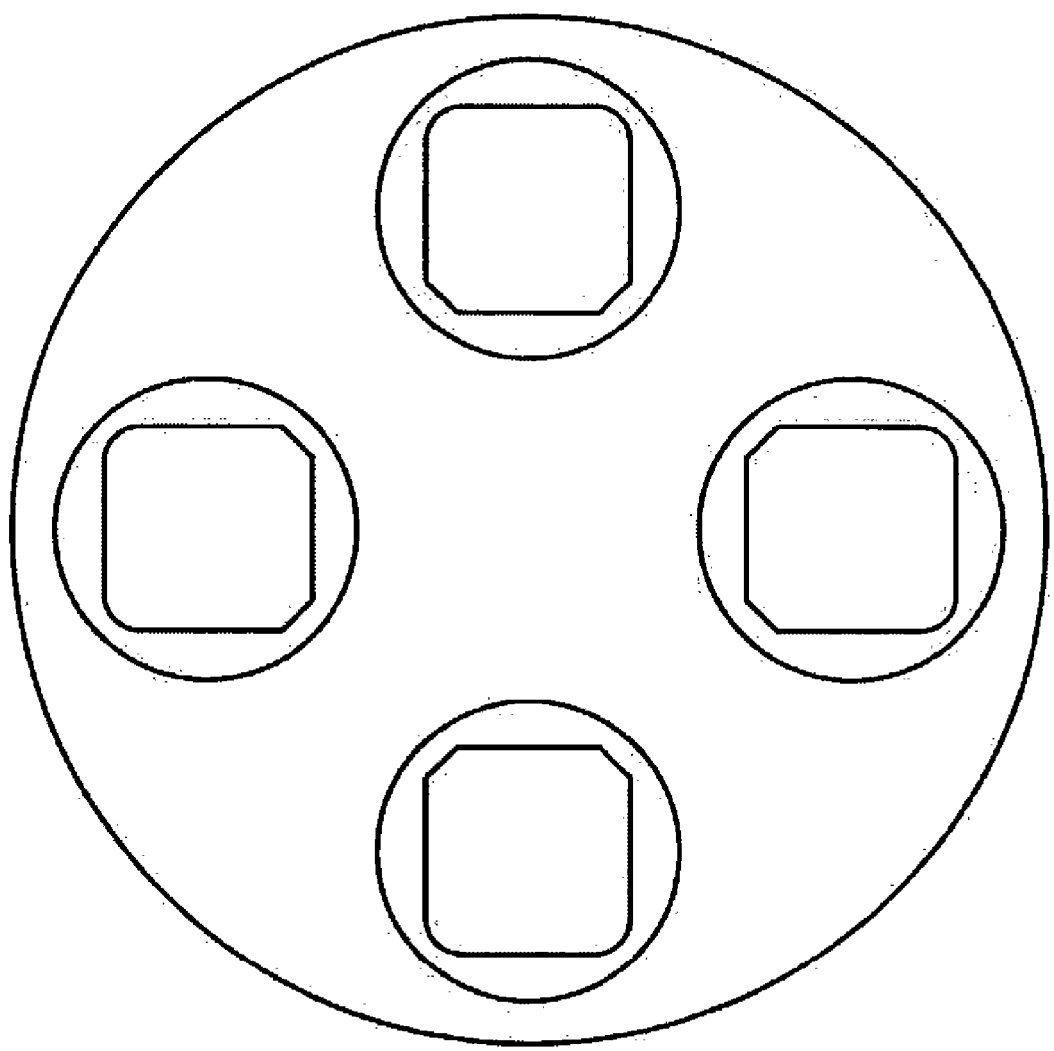
FIG. 12 is a top view of the external appearance of the preferred embodiment of the present invention.
Figure 13:
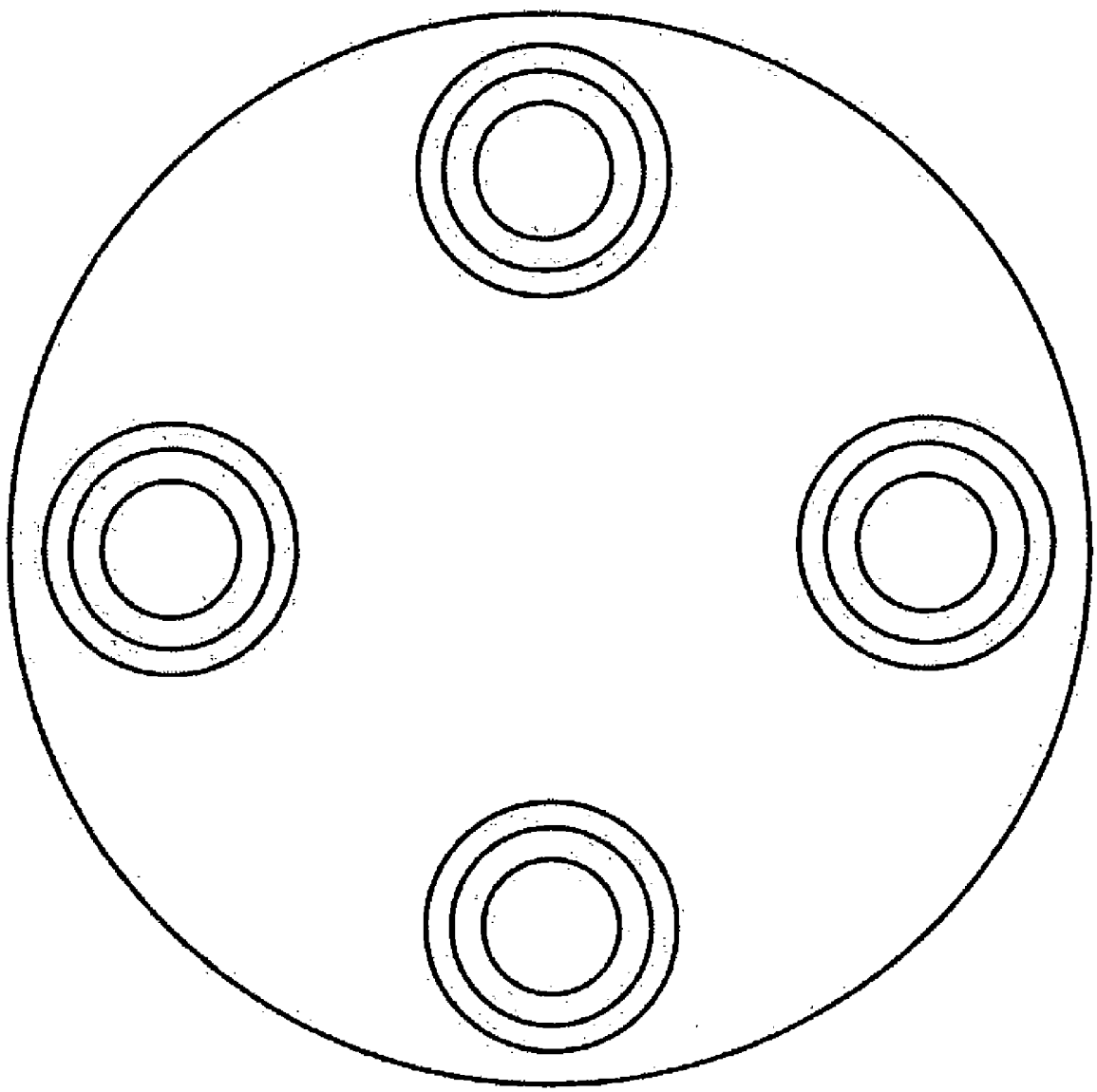
FIG. 13 is a bottom view of the external appearance of the preferred embodiment of the present invention.

FIG. 10 is a front perspective view of the external appearance of the preferred embodiment of the present invention. FIG. 11 is a rear perspective view of the external appearance of the preferred embodiment of the present invention. FIG. 12 is a top view of the external appearance of the preferred embodiment of the present invention. FIG. 13 is a bottom view of the external appearance of the preferred embodiment of the present invention.

Figure 14:
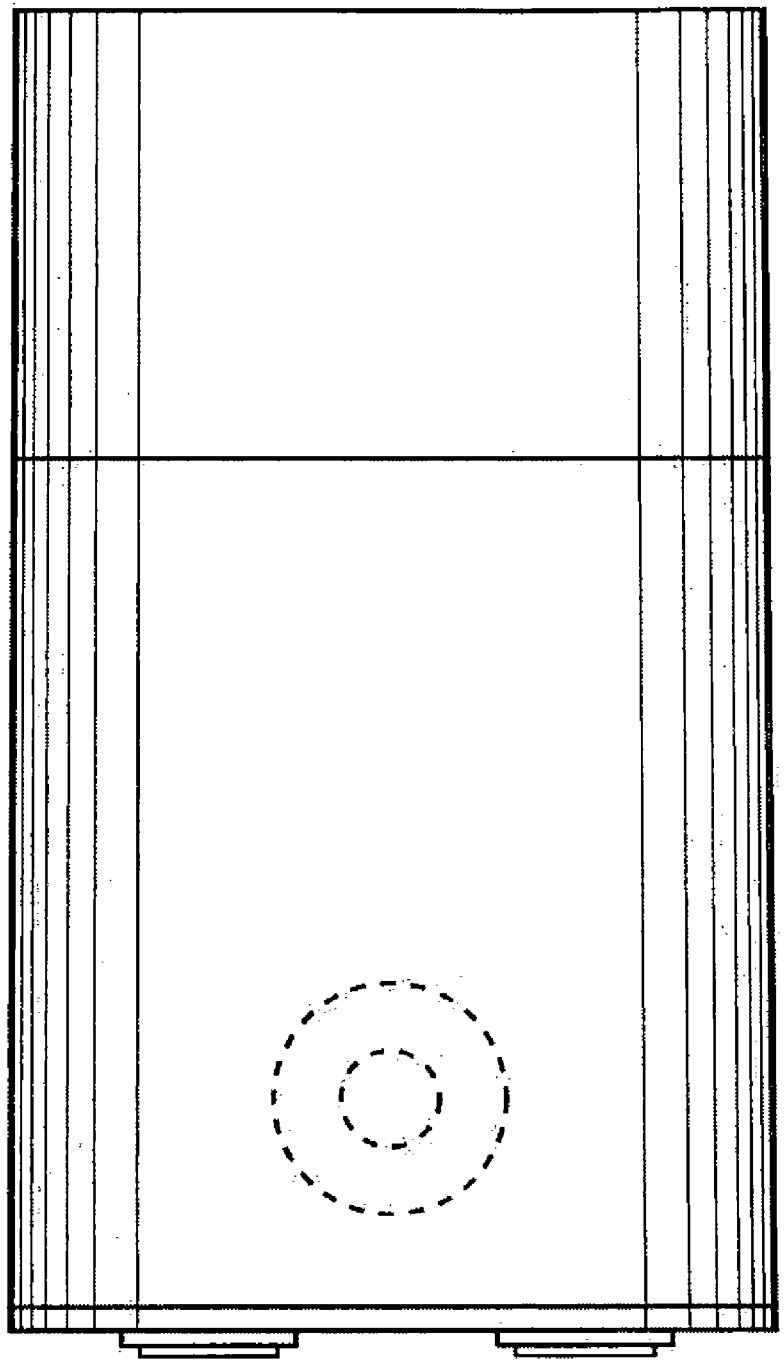
FIG. 14 is a front plan view of the external appearance of the preferred embodiment of the present invention.
Figure 15:
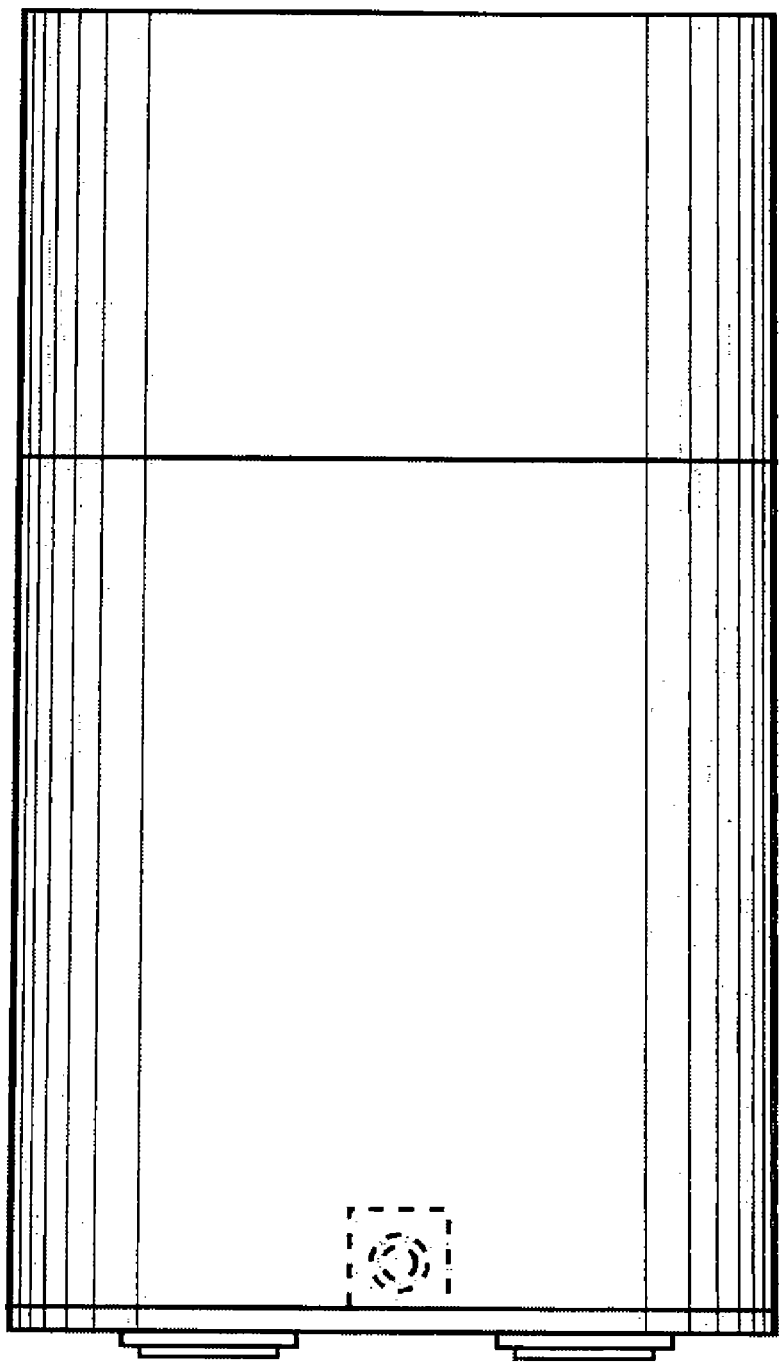
FIG. 15 is a rear plan view of the external appearance of the preferred embodiment of the present invention.
Figure 16:
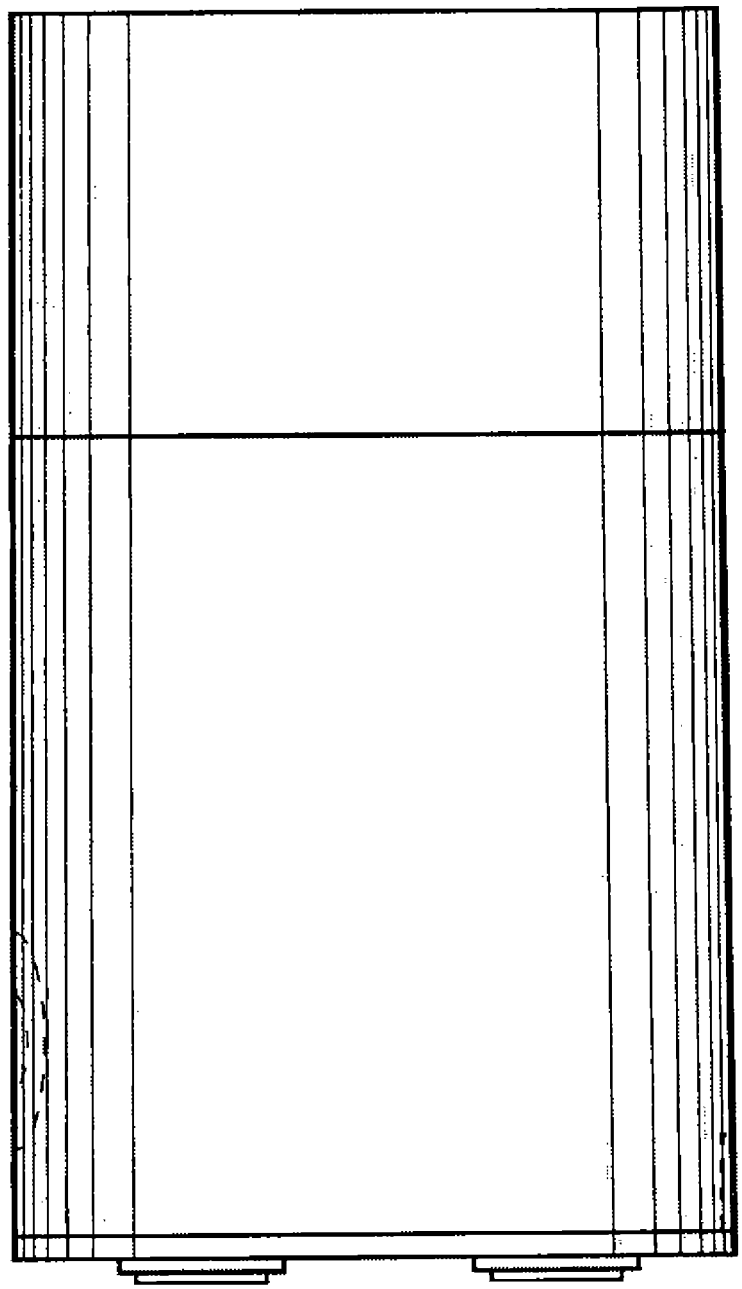
FIG. 16 is a right side plan view of the external appearance of the preferred embodiment of the present invention.
Figure 17:
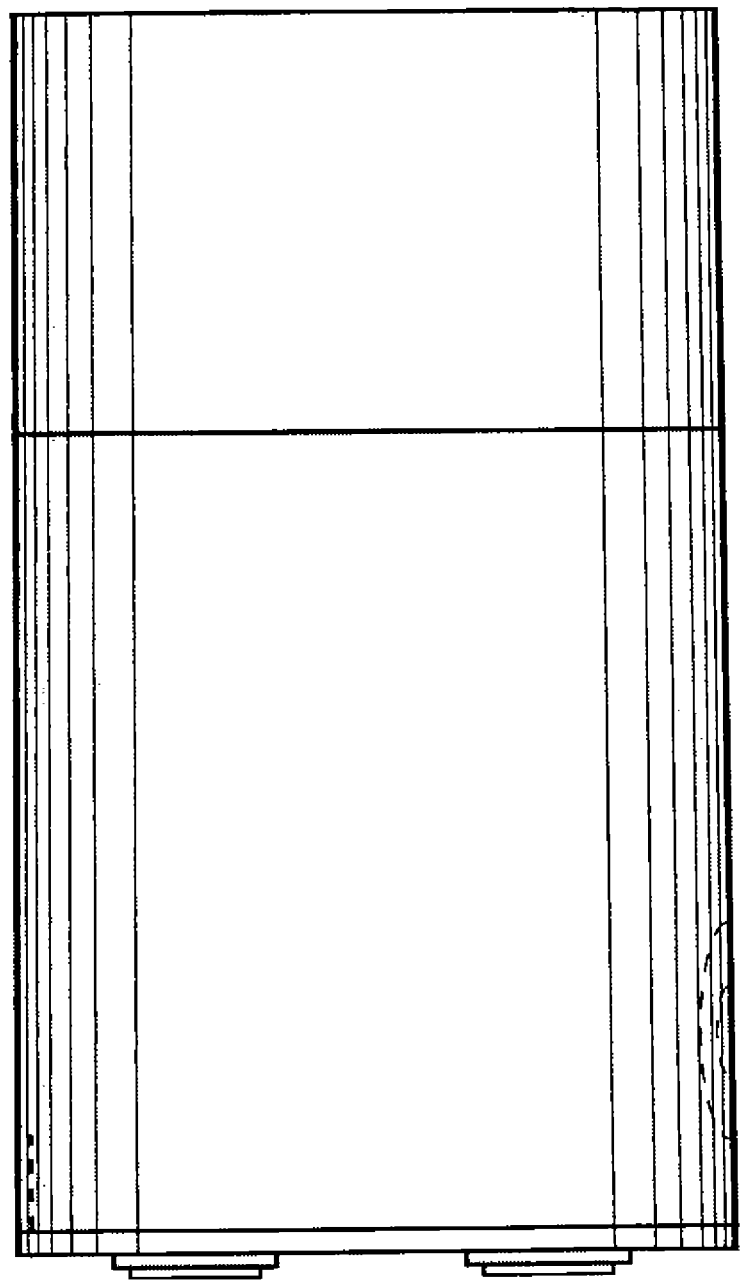
FIG. 17 is a left side plan view of the external appearance of the preferred embodiment of the present invention.
Figure 18:
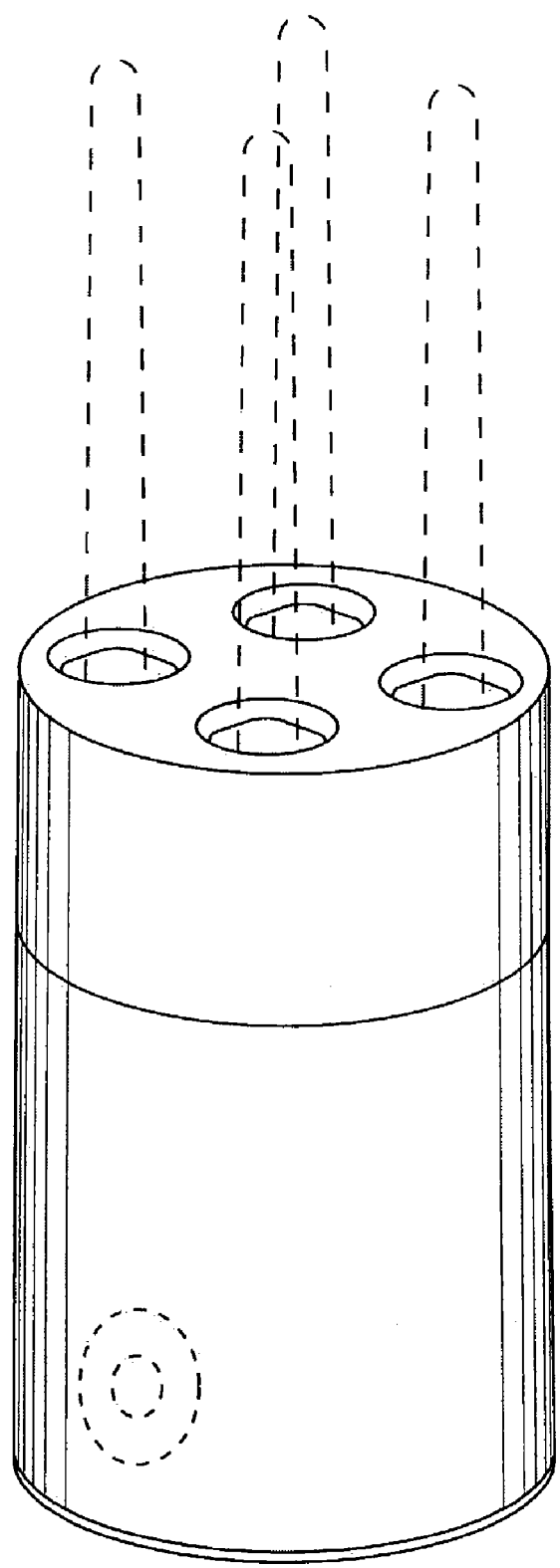
FIG. 18 is a front perspective view of the external appearance of the preferred embodiment of the present invention illustrated in its intended field of use.

FIG. 14 is a front plan view of the external appearance of the preferred embodiment of the present invention. FIG. 15 is a rear plan view of the external appearance of the preferred embodiment of the present invention. FIG. 16 is a right side plan view of the external appearance of the preferred embodiment of the present invention. FIG. 17 is a left side plan view of the external appearance of the preferred embodiment of the present invention. FIG. 18 is a front perspective view of the external appearance of the preferred embodiment of the present invention illustrated in its intended field of use.

As may be appreciated from the foregoing description, the present invention represents a significant improvement over the Prior Art devices. Many of the Prior Art devices cited above do not provide any safety features, or inadequate safety features, and as a result are not acceptable for consumer use. Devices such as the Andary device are too complex and difficult to clean, and also are unacceptable for consumer use. It is perhaps because of these concerns that an commercially successful UV toothbrush sanitizer has not emerged in the consumer market to date.

The present invention, in contrast, is simple and elegant in design, being made of only a few component parts. The safety system of the present apparatus allows the unit to be disassembled by the consumer for cleaning and the like, while maintaining UV safety. Moreover, the present invention can be adapted, via the adapter peg, to sanitize different types of items. In addition, the automatic operation of the present invention insures proper sanitation without user intervention.

While the preferred embodiment and various alternative embodiments of the invention have been disclosed and described in detail herein, it may be apparent to those skilled in the art that various changes in form and detail may be made therein without departing from the spirit and scope thereof.

I claim:

1. A sanitizing apparatus, comprising:
   a body for accepting at least one item to be sanitized, the body containing at least one germicidal lamp;
   a removable cap, removably attached to the body, the removable cap provided with at least one orifice to accepting the item to be sanitized, the removable cap having at least one extended member for extending into the body of the sanitizing apparatus; and
   a cutoff switch provided within the body of the sanitizing apparatus, coupled to at least one of the at least one extended member of the removable cap, such that when the removable cap is removed, the at least one germicidal lamp is extinguished,
   wherein the cutoff switch is located within the body of the sanitizing apparatus such that the cutoff switch cannot be activated by a user when the removable cap is removed.

2. The apparatus of claim 1, further comprising:
   a safety rod, slidably mounted within the body of the apparatus, the safety rod coupling the cutoff switch with at least one of the at least one extended member of the removable cap,
   wherein the body contains an orifice for accepting the safety rod so as to prevent a user from inserting a finger into the orifice to activate the cutoff switch.

3. The apparatus of claim 1, further comprising:
   a removable drip cup having a bottom portion for receiving and retaining fluids from a toothbrush, removably mounted within the body of the apparatus beneath the cap, such that when the cap is removed from the body of the apparatus, the removable drip cup may be removed for cleaning.

4. The apparatus of claim 3, wherein the removable drip cup surrounds at least a portion of the item to be sanitized and reflects at least a portion of light emitted from the germicidal lamp onto the item to be sanitized.

5. The apparatus of claim 3, further comprising a removable peg, slidably removable from the removable drip cup, the removable peg providing means to adjust the height of the item to be sanitized inserted into the apparatus.

6. The apparatus of claim 1, further comprising a control circuit, coupled to the germicidal lamp, for controlling actuation of the germicidal lamp such that, once activated, the germicidal lamp is activated for a first predetermined time period, and then shut off for a second predetermined time period.

7. The apparatus of claim 6, wherein the control circuit further activates the germicidal lamp for the first predetermined time period after the second predetermined time period has lapsed.

8. A sanitizing apparatus, comprising:
   a body for accepting at least one item to be sanitized, the body containing at least one germicidal lamp;
   a removable cap, removably attached to the body, the removable cap provided with at least one orifice to accepting the item to be sanitized,
   a removable drip cup having a bottom portion for receiving and retaining fluids from a toothbrush, removably mounted within the body of the apparatus beneath the cap, such that when the cap is removed from the body of the apparatus, the removable drip cup may he removed for cleaning; and
   a removable peg slidably removable from the removable drip cup the removable peg providing means to adjust the height of the item to be sanitized inserted into the apparatus.

9. The apparatus of claim 8, further comprising:
a control circuit, coupled to the germicidal lamp, for controlling actuation of the germicidal lamp such that, once activated, the germicidal lamp is activated for a first predetermined time period and then shut off for a second predetermined time period;
wherein the control circuit further activates the germicidal lamp for the first predetermined time period after the second predetermined time period has lapsed.

10. The sanitizing apparatus of claim 8, further comprising:
the removable cap having at least one extended member for extending into the body of the sanitizing apparatus;
a cutoff switch provided within the body of the sanitizing apparatus, coupled to at least one of the at least one extended member of the removable cap, such that when the removable cap is removed, the at least one germicidal lamp is extinguished, wherein the cutoff switch is located within the body of the sanitizing apparatus such that the cutoff switch cannot be activated by a user when the removable cap is removed; and
a safety rod, slidably mounted within the body of the apparatus, the safety rod coupling the cutoff switch with at least one of the at least one extended member of the removable cap, wherein the body contains an orifice for accepting the safety rod so as to prevent a user from inserting a finger into the orifice to activate the cutoff switch.

11. The apparatus of claim 8, further comprising:
a removable drip cup having a bottom portion for receiving and retaining fluids from a toothbrush, removably mounted within the body of the apparatus beneath the cap, such that when the cap is removed from the body of the apparatus, the removable drip cup may be removed for cleaning.

12. The apparatus of claim 11, wherein the removable drip cup surrounds at least a portion of the item to be sanitized and reflects at least a portion of light emitted from the germicidal lamp onto the item to be sanitized.

13. The apparatus of claim 11, further comprising a control circuit, coupled to the germicidal lamp, for controlling actuation of the germicidal lamp such that, once activated, the germicidal lamp is activated for a first predetermined time period and then shut off for a second predetermined time period.

14. A sanitizing apparatus, comprising:
a body for accepting at least one item to be sanitized, the body containing at least one germicidal lamp;
a removable cap, removably attached to the body, the removable cap provided with at least one orifice to accepting the item to be sanitized, the removable cap having at least one extended member for extending into the body of the sanitizing apparatus; and
a removable drip cup having a bottom portion for receiving and retaining fluids from a toothbrush, removably mounted within the body of the apparatus beneath the cap, such that when the cap is removed from the body of the apparatus, the removable drip cup may be removed for cleaning.

15. The apparatus of claim 14, wherein the removable drip cup surrounds at least a portion of the item to be sanitized and reflects at least a portion of light emitted from the germicidal lamp onto the item to be sanitized.

16. The apparatus of claim 15, further comprising a removable peg, slidably removable from the removable drip cup, the removable peg providing means to adjust the height of the item to be sanitized inserted into the apparatus.

17. The apparatus of claim 15, further comprising:
a control circuit, coupled to the germicidal lamp, for controlling actuation of the germicidal lamp such that, once activated, the germicidal lamp is activated for a first predetermined time period, and then shut off for a second predetermined time period.

18. The apparatus of claim 17, wherein the control circuit further activates the germicidal lamp for the first predetermined time period after the second predetermined time period has lapsed.

19. The sanitizing apparatus of claim 14, further comprising:
a cutoff switch provided within the body of the sanitizing apparatus, coupled to at least one of the at least one extended member of the removable cap, such that when the removable cap is removed, the at least one germicidal lamp is extinguished,
wherein the cutoff switch is located within the body of the sanitizing apparatus such that the cutoff switch cannot he activated by a user when the removable cap is removed.

20. The sanitizing apparatus of claim 19, further comprising:
a safety rod, slidably mounted within the body of the apparatus, the safety rod coupling the cutoff switch with at least one of the at least one extended member of the removable cap.
wherein the body contains an orifice for accepting the safety rod so as to prevent a user from inserting a finger into the orifice to activate the cutoff switch.

* * * * *